US012716893B2

(12) United States Patent
Zekeridou et al.

(10) Patent No.: US 12,716,893 B2
(45) Date of Patent: Aug. 25, 2026

(54) MATERIALS AND METHODS FOR DETECTING AND TREATING AUTOIMMUNE MOVEMENT DISORDERS

(71) Applicant: Mayo Foundation for Medical Education and Research, Rochester, MN (US)

(72) Inventors: Anastasia Zekeridou, Rochester, MN (US); Andrew McKeon, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1171 days.

(21) Appl. No.: 17/603,515

(22) PCT Filed: Apr. 13, 2020

(86) PCT No.: PCT/US2020/027933

§ 371 (c)(1),
(2) Date: Oct. 13, 2021

(87) PCT Pub. No.: WO2020/214528

PCT Pub. Date: Oct. 22, 2020

(65) Prior Publication Data

US 2022/0187294 A1 Jun. 16, 2022

Related U.S. Application Data

(60) Provisional application No. 62/835,252, filed on Apr. 17, 2019.

(51) Int. Cl.

| | |
|---|---|
| ***G01N 33/564*** | (2006.01) |
| ***A61K 31/56*** | (2006.01) |
| ***A61P 25/28*** | (2006.01) |
| ***C12N 9/16*** | (2006.01) |
| ***C12Q 1/44*** | (2006.01) |
| ***G01N 33/68*** | (2006.01) |

(52) U.S. Cl.

CPC ........... *G01N 33/564* (2013.01); *A61K 31/56* (2013.01); *A61P 25/28* (2018.01); *C12N 9/16* (2013.01); *C12Q 1/44* (2013.01); *G01N 33/6896* (2013.01); *C12Y 301/04017* (2013.01); *G01N 2333/916* (2013.01); *G01N 2800/24* (2013.01); *G01N 2800/2835* (2013.01)

(58) Field of Classification Search

CPC ............. G01N 33/564; G01N 33/6896; G01N 2800/24; G01N 2333/916; G01N 2800/2835; A61P 25/28; A61K 31/56; C12N 9/16; C12Q 1/44; C12Y 301/04017

See application file for complete search history.

(56) References Cited

U.S. PATENT DOCUMENTS

| | | | |
|---|---|---|---|
| 6,100,037 | A | 8/2000 | Phillips et al. |
| 10,039,764 | B2 | 8/2018 | Piazza |
| 2004/0152106 | A1 | 8/2004 | Robertson et al. |
| 2006/0110783 | A1 | 5/2006 | Golz et al. |
| 2013/0071860 | A1 | 3/2013 | Hale et al. |
| 2013/0266963 | A1 | 10/2013 | Hauenstein et al. |

FOREIGN PATENT DOCUMENTS

| | | |
|---|---|---|
| WO | WO 2018/048884 | 3/2018 |
| WO | WO 2018/063792 | 4/2018 |

OTHER PUBLICATIONS

EP Extended Search Report in European Appln. No. 20791987.9, dated Apr. 8, 2022, 7 pages.

O'Connor et al., "GABAA Receptor Autoimmunity," Neurol. Neuroimmunol. Neuroinflammation, 6(3):e552, Apr. 4, 2019, 6 pages.

Williams et al., "Association of Autoimmune Encephalitis With Combined Immune Checkpoint Inhibitor Treatment for Metastatic Cancer," JAMA Neurology, 73(8):928-933, Jun. 6, 2016.

Zekeridou et al., "Paraneoplastic phosphodiesterase 10a neurological autoimmunity unmasked by immune checkpoint inhibitor therapy," Abstract, Presented at Proceedings of the 71st Annual Meeting of the American Academy of Neurology, Philadelphia, PA, USA, May 4-10, 2019; Neurology, 92(15S):S21.002, Apr. 2019, 2 pages.

Balint et al., "Movement disorders with neuronal antibodies: Syndromic approach, genetic parallels and pathophysiology," Brain, Jan. 1, 2018, 141(1):13-36.

Basal et al., "Paraneoplastic neuronal intermediate filament autoimmunity," Neurology, Oct. 3, 2018, 91(18):e1677-e1689.

Binks et al., "LGII, CASPR2 and related antibodies: a molecular evolution of the phenotypes," J. Neurol. Neurosurg. Psychiatry, May 2018, 89(5):526-534.

Cox et al., "Tissue subcellular fractionation and protein extraction for use in mass-spectrometry-based proteomics," Nat. Protocols, Nov. 22, 2006, 1(4):1872-1878.

Crisp et al., "Autoimmune synaptopathies," Nat. Rev. Neuroscience, Jan. 25, 2016, 17(2):103-117.

Dalmau et al., "Autoantibodies to Synaptic Receptors and Neuronal Cell Surface Proteins in Autoimmune Diseases of the Central Nervous System," Physiol. Reviews, Apr. 2017, 97(2):839-887.

Damato et al., "The clinical features, underlying immunology, and treatment of autoantibody-mediated movement disorders," Mov. Disorders, Sep. 2018, 33(9):1376-1389.

Diggle et al., "Biallelic Mutations in PDE10A Lead to Loss of Striatal PDE10A and a Hyperkinetic Movement Disorder with Onset in Infancy," Am. J. Hum. Genetics, Apr. 7, 2016, 98(4):735-743.

(Continued)

*Primary Examiner* — Olga N Chernyshev
(74) *Attorney, Agent, or Firm* — Fish & Richardson P.C.

(57) ABSTRACT

Materials and methods are provided herein for detecting the presence of an autoantibody specific for PDE10A to identify the mammal as having an autoimmune neurological disorder as well as methods and materials for treating an autoimmune neurological disorder. Materials and methods also are provided herein for treating cancer and/or neurological autoimmunity in a mammal using an immune checkpoint inhibitor and detecting the presence of an autoantibody specific for PDE10A to monitor for the development of neurologic complications in the mammal.

5 Claims, 3 Drawing Sheets

(56) References Cited

OTHER PUBLICATIONS

Fang et al., "Autoimmune Glial Fibrillary Acidic Protein Astrocytopathy: A Novel Meningoencephalomyelitis," JAMA Neurology, Nov. 1, 2016, 73(11):1297-1307.
Fazio et al., "Patterns of age related changes for phosphodiesterase type-10A in comparison with dopamine D 2/3 receptors and sub-cortical volumes in the human basal ganglia: A PET study with 18F-MNI-659 and 11 C-raclopride with correction for partial vol. effect," Neuroimage, May 15, 2017, 152:330-339.
Fujishige et al., "Cloning and characterization of a novel human phosphodiesterase that hydrolyzes both cAMP and cGMP (PDE10A)," J. Biol. Chemistry, Jun. 25, 1999, 274(26):18438-18445.
Gadoth et al., "Microtubule-associated protein IB: Novel paraneoplastic biomarker," Ann. Neurology, Feb. 2017, 81(2):266-277.
GenBank Accession No. NM_001130690.2, "*Homo sapiens* phosphodiesterase 10A (PDE10A), transcript variant 1, mRNA," dated Apr. 2, 2018, 7 pages.
GenBank Accession No. NM_006661.3, "*Homo sapiens* phosphodiesterase 10A (PDE10A), transcript variant 2, mRNA," dated Apr. 5, 2018, 7 pages.
Gozzard et al., "Novel Humoral Prognostic Markers in Small-Cell Lung Carcinoma: A Prospective Study," PLoS One, Nov. 25, 2015, 10(11):e0143558, 14 pages.
Gozzard et al., "Paraneoplastic neurologic disorders in small cell lung carcinoma: A prospective study," Neurology, Jul. 21, 2015, 85(3):235-240.
Honorat et al., "Autoimmune Movement Disorders: a Clinical and Laboratory Approach," Curr. Neurol. Neurosci. Reports, Jan. 24, 2017, 17(1):4, 11 pages.
Honorat et al., "Autoimmune septin-5 cerebellar ataxia," Neurol. Neuroimmunol. Neuroinflammation, Sep. 2018, 5(5):e474, 6 pages.
Hottinger, "Neurologic complications of immune checkpoint inhibitors," Curr. Opin. Neurology, Dec. 2016, 29(6):806-812.
Iorio et al., "Neural antigen-specific autoimmune disorders," Immunological Reviews, Jul. 2012, 248(1):104-121.
Joseph et al., "Association of the autoimmune disease scleroderma with an immunologic response to cancer," Science, Jan. 10, 2014, 343(6167):152-157.
Kao et al., "Neurological Complications Associated With Anti-Programmed Death 1 (PD-1) Antibodies," JAMA Neurology, Oct. 1, 2017, 74(10):1216-1222.
Kotera et al., "Subcellular localization of cyclic nucleotide phosphodiesterase type 10A variants, and alteration of the localization by cAMP-dependent protein kinase-dependent phosphorylation," J. Biol. Chemistry, Feb. 6, 2004, 279(6):4366-4375.
Lancaster et al., "Neuronal autoantigens-pathogenesis, associated disorders and antibody testing," Nat. Rev. Neurology, Jun. 19, 2012, 8(7):380-390.
Loughney et al., "Isolation and characterization of PDE10A, a novel human 3', 5'-cyclic nucleotide phosphodiesterase," Gene, Jun. 14, 1999, 234(1):109-117.
Mammen et al., "Pre-existing antiacetylcholine receptor autoantibodies and B cell lymphopaenia are associated with the development of myositis in patients with thymoma treated with avelumab, an immune checkpoint inhibitor targeting programmed death-ligand 1," Ann. Rheum. Diseases, Jan. 2019, 78(1):150-152.
Masilamoni et al., "Effects of a novel phosphodiesterase 10A inhibitor in non-human primates: a therapeutic approach for schizophrenia with improved side effect profile," Neuropharmacology, Nov. 2016, 110(Part A):449-457.
McKeon et al., "Paraneoplastic encephalomyelopathies: Pathology and mechanisms," Acta Neuropathologica, Sep. 22, 2011, 122(4):381-400.
Miyatake et al., "A familial case of PDE10A-associated childhood-onset chorea with bilateral striatal lesions," Mov. Disorders, Jan. 2018, 33(1):177-179.
Niccolini et al., "Altered PDE10A expression detectable early before symptomatic onset in Huntington's disease," Brain, Oct. 2015, 138(10):3016-3029.
Niccolini et al., "PDE10A and ADCY5 mutations linked to molecular and microstructural basal ganglia pathology," Mov. Disorders, Dec. 2018, 33(12):1961-1965.
O'Toole et al., "Autoimmune chorea in adults," Neurology, Mar. 19, 2013, 80(12):1133-1144.
Palapattu et al., "Paraneoplastic syndromes in urologic malignancy: the many faces of renal cell carcinoma," Rev. Urology, 2002, 4(4):163-170.
PCT International Preliminary Report on Patentability in International Appln. No. PCT/US2020/027933, dated Sep. 28, 2021, 6 pages.
PCT International Search Report and Written Opinion in International Appln. No. PCT/US2020/027933, dated Jul. 22, 2020, 8 pages.
Seeger et al., "Immunohistochemical localization of PDE10A in the rat brain," Brain Research, Sep. 26, 2003, 985(2):113-126.
Small et al., "Genetic alterations and tumor immune attack in Yo paraneoplastic cerebellar degeneration," Acta Neuropathologica, Apr. 2018, 135(4):569-579.
Soderling et al., "Isolation and characterization of a dual-substrate phosphodiesterase gene family: PDE10A," Proc. Natl. Acad. Sci. USA, Jun. 8, 1999, 96(12):7071-7076.
Touat et al., "Neurological toxicities associated with immune-checkpoint inhibitors," Curr. Opin. Neurology, Dec. 2017, 30(6):659-668.
Vernino et al., "Paraneoplastic Chorea Associated with CRMP-5 Neuronal Antibody and Lung Carcinoma," Ann. Neurology, May 2002, 51(5):625-630.
Wilson et al., "Emerging biology of PDE10A," Curr. Pharm. Des., 2015, 21(3):378-388.
Wilson et al., "Molecular Imaging Markers to Track Huntington's Disease Pathology," Front. Neurology, Jan. 30, 2017, 8:11, 11 pages.
Xie et al., "Cellular and subcellular localisation of PDEI0A, a striatum enriched phosphodiesterase," Neuroscience, May 12, 2006, 139(2):597-607.
Zekeridou et al. "Phosphodiesterase 10A IgG, a novel biomarker of paraneoplastic neurologic autoimmunity", Neurology, Aug. 20, 2019, 93(8):e815-e822.
Zekeridou et al., "Frequency of synaptic autoantibody accompaniments and neurological manifestations of thymoma," JAMA Neurology, Jul. 1, 2016, 73(7):853-859.
Zekeridou et al., "Mutated cancer autoantigen implicated cause of paraneoplastic myasthenia gravis." Muscle Nerve, Oct. 2018, 58(4):600-604.

250 kD
150 kD
100 kD
75 kD
50 kD
Normal
Normal
Patient 5
Patient 4B
Patient 3
Patient 4A
Patient 2
Patient 1
Normal
Patient's serum
IgG elution A
Striatum
PDE10A-IgG
Patient-IgG
Merged
B
250 kD
150 kD
100 kD
75 kD
50 kD
Normal
Normal
Patient 1
Patient 2
Patient 3
Patient 4A
Patient 4B
Patient 5
Normal
Normal
Normal
Normal
Normal
Normal
Normal
C
PDE10A1 cells
PDE10A2 cells
PDE10A2 cells
Control-IgG
D
PDE10A-IgG patient
PCA1 patient
Post PDE10A absorption

MATERIALS AND METHODS FOR DETECTING AND TREATING AUTOIMMUNE MOVEMENT DISORDERS

CROSS-REFERENCE TO RELATED APPLICATIONS

This application is a National Stage application under 35 U.S.C. § 371 of International Application No. PCT/US2020/027933, having an International Filing Date of Apr. 13, 2020, which claims priority to U.S. Application Ser. No. 62/835,252, filed Apr. 17, 2019. The disclosures of the prior applications are considered part of (and are incorporated by reference in) the disclosure of this application.

BACKGROUND

Technical Field

This document relates to materials and methods for identifying and/or treating an autoimmune movement disorder or other signs of neurological autoimmunity. For example, this document provides materials and methods for detecting the presence of an autoantibody specific for PDE10A to identify the mammal as having neurological autoimmunity manifesting mainly as a movement disorder as well as methods for treating a mammal having a PDE10A antibody related neurological autoimmunity.

This document also provides materials and methods for treating neurological autoimmunity and/or cancer in a mammal with prior use of immune checkpoint inhibitor blockade and detectable autoantibodies specific for PDE10A and monitoring for the development of neurologic complications in the mammal.

Background Information

A paraneoplastic neurologic disorder (PND) results from the indirect effect of an anti-tumor immune response on the nervous system or muscle without local invasion or metastasis. See, Gozzard, et al., *Neurology* 2015; 85:235-239. Manifestations of neurological paraneoplastic autoimmunity can involve any level of the neuraxis. See, for example, McKeon and Pittock, Acta Neuropathol 2011; 122:381-400; and Lancaster and Dalmau, *Nat Rev Neurol* 2012; 8:380-390. Autoimmune movement disorders and encephalopathy have been described in a paraneoplastic context. See, for example, Honorat and McKeon, *Curr Neurol Neurosci Rep* 2017; 17:4; Damato et al., *Mov Disord* 2018; 33:1376-1389; and Balint, et al., *Brain,* 2018; 141:13-36.

Small-cell lung cancer and thymoma are two cancers commonly associated with PNDs. See, e.g., Gozzard, et al., 2015, supra; and Zekeridou, et al., *JAMA Neurol* 2016; 73:853-859. Immune checkpoint inhibitors used for treating cancer are typically monoclonal antibodies that neutralize negative regulatory steps in T-cell immune responses, and can augment anti-tumor immunity. As a consequence, there can be an increase in autoimmune complications.

SUMMARY

This document is based, at least in part, on the discovery of an autoantibody biomarker specific for PDE10A in patients with movement disorders (e.g., presenting mostly with movement disorders), expanding the spectrum of diagnosable paraneoplastic central nervous system (CNS) disorders. As described herein, patients with autoantibodies specific for PDE10A produced identical basal ganglia-predominant synaptic staining of murine brain tissue by indirect immunofluorescence. The autoantigen was identified by immunoprecipitation and mass spectrometry as PDE10A, and confirmed by antigen-specific recombinant western blot and cell-based assays, and immune absorption experiments. Most of the patients had a movement disorder and had cancer. Accordingly, this document provides materials and methods for detecting the presence of an autoantibody specific for PDE10A to identify a mammal as having PDE10A-antibody-related neurological autoimmunity. This document also provides methods and materials for treating mammals having an autoimmune movement disorder that were identified as having the presence of an autoantibody specific for PDE10A. In addition, this document provides methods and materials for treating cancer and/or neurological autoimmunity in a mammal with prior use of immune checkpoint inhibitors in a manner that the detection of an autoantibody specific for PDE10A guides treatment and/or assists in monitoring that mammal for the development of neurologic complications. Early diagnosis and treatment with appropriate immunotherapy can prevent further neurological deterioration.

In one aspect, this document features a method for detecting an autoimmune neurological disorder in a mammal or serological evidence thereof. The method comprises (or consists essentially of, or consists of) (a) detecting, in a biological sample obtained from the mammal, the presence of an autoantibody specific for PDE10A, and (b) classifying the mammal as having the autoimmune neurological disorder or the serological evidence. The mammal can be a human. The method can comprise classifying the mammal as having the autoimmune neurological disorder. The method can comprise classifying the mammal as having the serological evidence. The biological sample can be a tissue sample, a blood sample, a serum sample, a CSF sample, or a plasma sample.

In another aspect, this document features a method for treating a mammal having an autoimmune neurological disorder. The method comprises (or consists essentially of, or consists of) (a) detecting the presence of an autoantibody specific for PDE10A in a sample obtained from the mammal, and (b) administering a steroid to the mammal. The mammal can be a human. The biological sample can be a tissue sample, a blood sample, a serum sample, a CSF sample, or a plasma sample.

In another aspect, this document features a method for treating an autoimmune neurological disorder. The method comprises (or consists essentially of, or consists of) administering a steroid to a mammal having the autoimmune neurological disorder and identified as having an autoantibody specific for PDE10A. The mammal can be a human.

In another aspect, this document features a method for treating a mammal having cancer. The method comprises (or consists essentially of, or consists of) (a) administering an immune checkpoint inhibitor (ICI) to the mammal; (b) detecting the presence or absence of an autoantibody specific for PDE10A in a sample obtained from the mammal; and (c) repeating steps (a) and (b) if the absence is detected and discontinuing steps (a) and (b) if the presence is detected. The mammal can be a human. The biological sample can be a tissue sample, a blood sample, a serum sample, a CSF sample, or a plasma sample. The method can comprise detecting the presence. The method can comprise administering a steroid to the mammal.

In another aspect, this document features a method for reducing development of neurological autoimmunity in a mammal, wherein the mammal is undergoing ICI therapy at a dose and frequency. The method comprises (or consists essentially of, or consists of) (a) detecting the presence or absence of an autoantibody specific for PDE10A in a sample obtained from the mammal; (b) reducing the dose or the frequency of the ICI therapy if the presence is detected; and (c) maintaining or increasing the dose of the ICI therapy and maintaining or increasing the frequency of the ICI therapy if the absence is detected. The mammal can be a human. The biological sample can be a tissue sample, a blood sample, a serum sample, a CSF sample, or a plasma sample.

Unless otherwise defined, all technical and scientific terms used herein have the same meaning as commonly understood by one of ordinary skill in the art to which this disclosure pertains. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
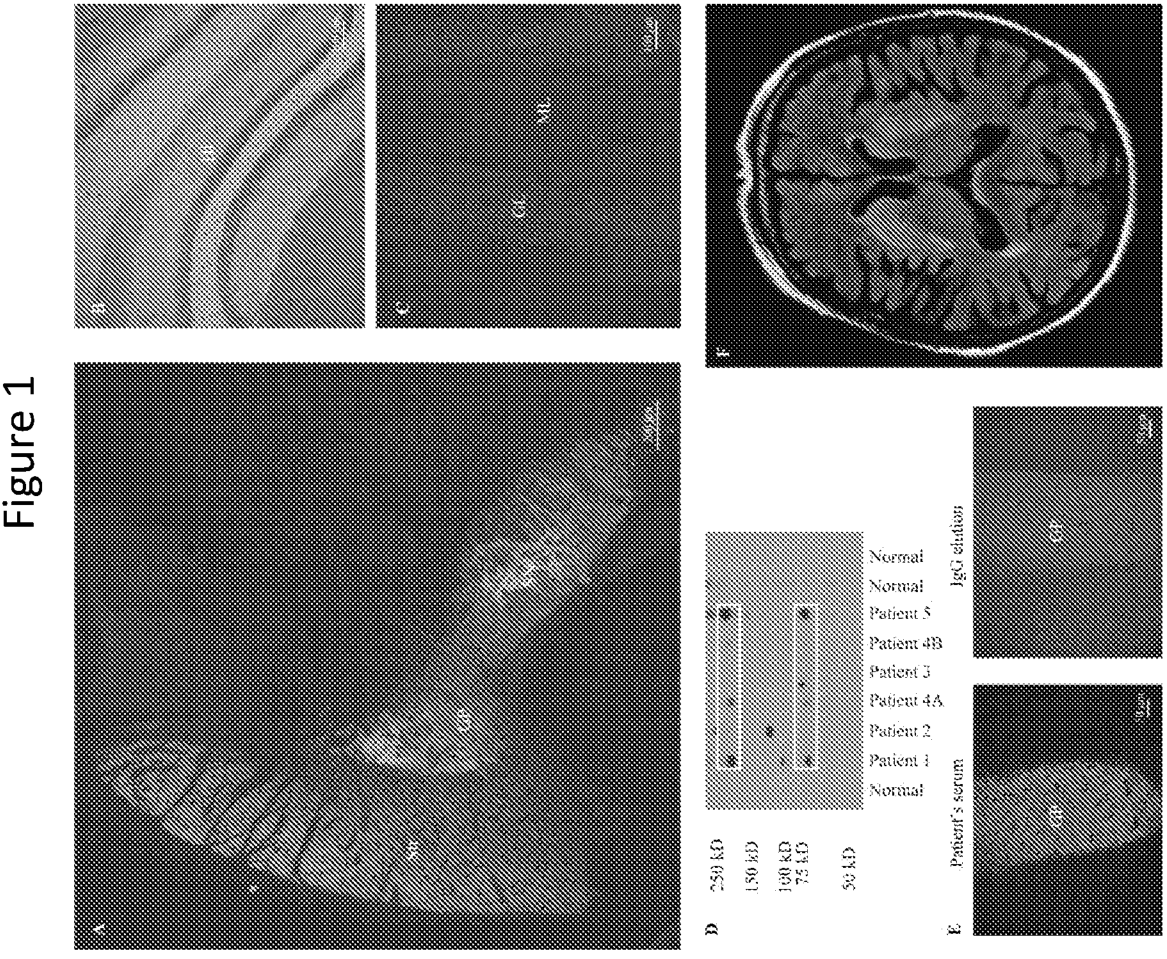
FIGS. 1A-1F. Detection of the patients with PDE10A autoantibody. Indirect immunofluorescence assay performed on murine tissue with patient serum demonstrates synaptic staining of the basal ganglia (A), more prominent than the hippocampus (B) and to a lesser extent the granular layer of the cerebellum (C). Western blot probing of lysed membrane fraction of pig basal ganglia with serum IgG of 3 patients identified an immunoreactive band ~75 kDa and another >200 kDa, that were not seen with normal control serum IgGs (D) Elution of patient 1's IgG from the corresponding 75 kDa nitrocellulose reproduced the original tissue staining pattern when applied to mouse brain as the patient's serum (E), while an IgG elution from a control band (~150 kDa) did not (not shown). T2 fluid activated inversion recovery (FLAIR) MRI image of patient 4 with bilateral basal ganglial hyperintensities (F). GL: granular layer, GP: globus pallidus, Hi: Hippocampus, ML: molecular layer, SN: substantia nigra, Str: striatum FIGS. 2A-2D. Antigen characterization. (A) Rabbit PDE10A-IgG (green), co-localizes with patient serum IgG (red) by confocal indirect immunofluorescence imaging on murine basal ganglia (merged images; yellow). Nuclei are blue (DAPI stained). (B) Recombinant PDE10A Western blot of 5 patients (6 sera, patient 4 had sera from 2 time-points) and normal controls. Interestingly, the two patients whose serum lacked 75 kDa reactivity in WB testing with pig basal ganglia extracts (FIG. 1D) were positive by recombinant WB but yielded a less intense signal than the other patients' sera. (C) Cell-based indirect immunofluorescence, commercial PDE10A-IgG (green), patient's serum (red) and merged images (yellow); nuclear staining in blue (DAPI). (D) Immune absorption of PDE10A-IgG-positive patient's serum with 2 μg of recombinant PDE10A protein eliminates the basal ganglia staining by indirect immunofluorescence while the control PCA1-IgG-positive serum's staining in the perikarya of cerebellar Purkinje neurons is unchanged when absorbed with the same amount of recombinant PDE10A protein. PDE10A: phosphodiesterase 10A, PCA1: Purkinje-cell cytoplasmic antibody 1.
Figure 2:
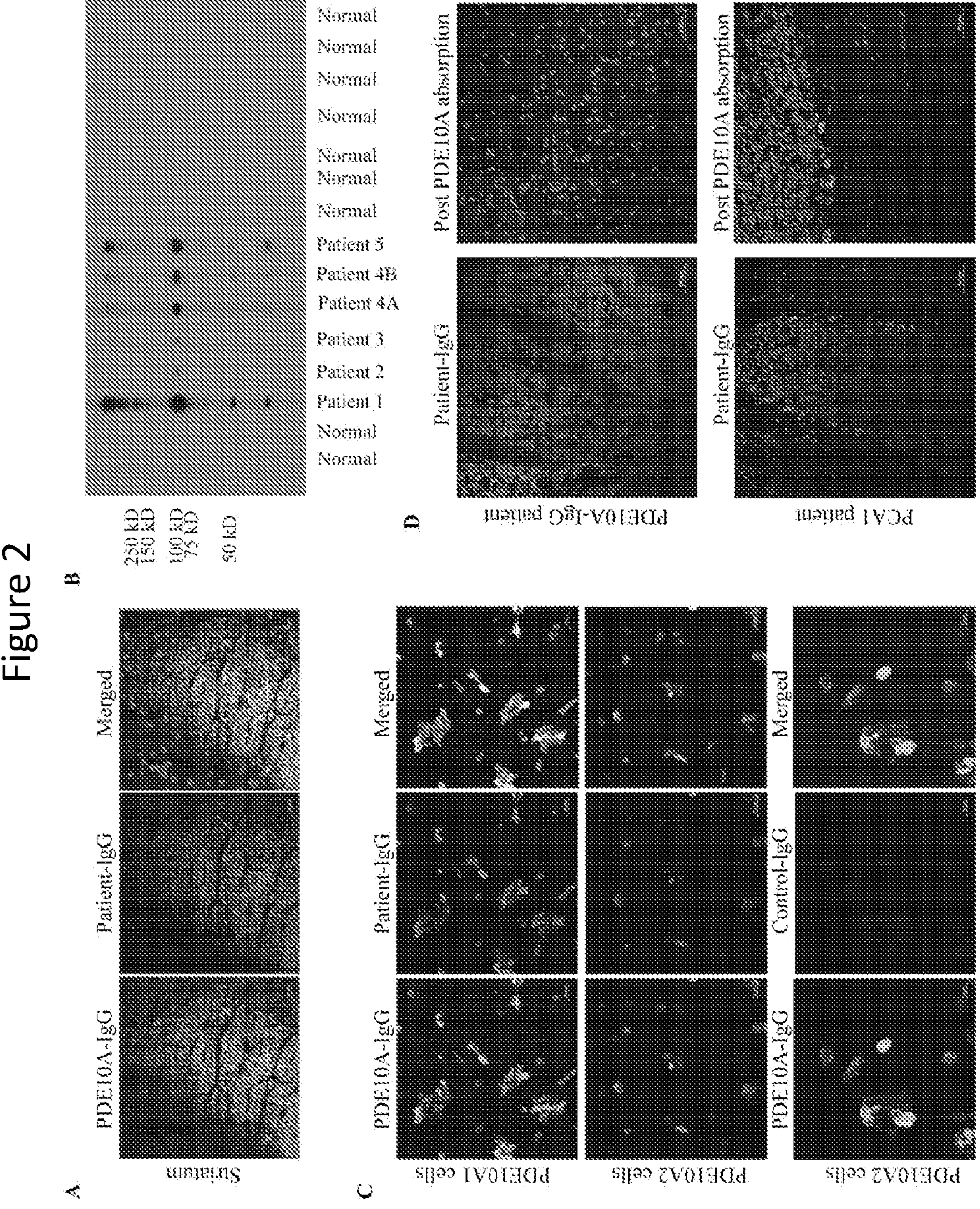

As described herein, an IgG autoantibody marker was identified in the serum of individuals presenting with movement disorders, with or without co-existing encephalopathy. The target of the autoantibody was identified as phosphodiesterase 10A (PDE10A), a dual-substrate, cyclic nucleotide phosphodiesterase that hydrolyzes adenosine and guanosine 3',5'-cyclic monophosphates. PDE10A is an intracellular protein that has two isoforms, PDE10A1 and PDE10A2. PDE10A1 is membrane-bound, while PDE10A2 is found in the cytoplasm. Thus, this document provides materials and methods for detecting PDE10A-specific autoantibodies in a mammal that presents with an autoimmune central nervous system (CNS) disorder.

Furthermore, as described herein, this document provides materials and methods for treating a mammal having a paraneoplastic CNS disorder such as a movement disorder. Any appropriate mammal can be treated as described herein including, without limitation, humans, monkeys, dogs, horses, sheep, pigs, goats, rabbits, rats, or mice. For example, in treating a mammal (e.g., a human) having a paraneoplastic CNS disorder (e.g., a movement disorder) that was identified as having PDE10A-specific autoantibodies present in a biological sample obtained from the mammal, the mammal (e.g., human) can be administered a steroid if not otherwise contra-indicated. In some cases, in treating a mammal (e.g., a human) having cancer with an immune checkpoint inhibitor, the presence or absence of PDE10A-specific autoantibodies in a biological sample from the mammal can be used to monitor that mammal for risk of developing neurological complications (e.g., a movement disorder) or identifying neurological complications associated with the immune checkpoint inhibitor therapy in order to guide appropriate treatment both for cancer and neurological autoimmunity. Examples of immune checkpoint inhibitors can include, without limitation, anti-PD1 antibodies (e.g., Pembrolizumab or Nivolumab), anti-CTLA4 antibodies (e.g., Ipilimumab), anti-PDL1 antibodies (e.g., Avelumab, Atezolizumab, or Durvalumab), and anti-PDL2 antibodies, among others.

Detecting PDE10A Autoantibodies

PDE10A polypeptides can be used in the methods described herein to detect a PDE10A-specific autoantibody. PDE10A polypeptides may be obtained, for example, from human, mice, or transfected cells (e.g., mammalian, *E. coli* or yeast cells) expressing a recombinant PDE10A nucleic acid, or a PDE10A polypeptide may be synthetic. An example of a PDE10A polypeptide sequence (and the nucleic acid encoding such a polypeptide) can be found in GenBank Accession No. NM_001130690.2. Recombinant human PDE10A protein also is commercially available. See, for example, Abcam, product ab198428.

PDE10A polypeptides can be purified. A "purified" polypeptide refers to a polypeptide that constitutes the major component in a mixture of components, e.g., 30% or more, 40% or more, 50% or more, 60% or more, 70% or more, 80% or more, 90% or more, 95% or more, or 99% or more by weight. Polypeptides may be purified by methods including affinity chromatography or immunosorbant affinity column. Such methods can be modified to increase the solubility of the polypeptide, and purified polypeptides can be examined for their immunogenicity.

PDE10A polypeptides or fragments thereof can be used with or without modification for the detection of PDE10A-specific antibodies such as PDE10A-specific autoantibodies. Polypeptides can be labeled by either covalently or non-covalently combining the polypeptide with a second substance that provides for detectable signal. A wide variety of labels and conjugation techniques can be used. Non-limiting examples of suitable labels include radioisotopes, enzymes, substrates, cofactors, inhibitors, fluorescers, chemiluminescers, and magnetic particles.

PDE10A polypeptides or fragments thereof can be used in various immunological techniques to detect PDE10A-specific antibodies in a biological sample from the mammal. For example, PDE10A polypeptides can be used in an immunoassay to detect PDE10A-specific autoantibodies in a biological sample. PDE10A polypeptides used in an immunoassay can be in a cell lysate (e.g., a whole cell lysate or a cell fraction), or purified PDE10A polypeptides or fragments thereof can be used, provided at least one antigenic site recognized by PDE10A-specific antibodies (e.g., PDE10A-specific autoantibodies) remains available for binding. Depending on the nature of the sample, either or both immunoassays and immunocytochemical staining techniques may be used. Enzyme-linked immunosorbent assays (ELISA), Western blot, and radioimmunoassays can be used to detect the presence of PDE10A-specific autoantibodies in a biological sample from a mammal (e.g., a human). Non-limiting examples of biological samples include blood, serum, plasma, or cerebrospinal fluid. Additionally, solid tissues, for example, spinal cord or brain biopsies can be used.

As used herein, nucleic acid (e.g., a nucleic acid encoding a PDE10A polypeptide) refers to RNA or DNA. As used herein with respect to nucleic acids, "isolated" refers to (i) a nucleic acid sequence encoding part or all of PDE10A polypeptide, but free of coding sequences that normally flank one or both sides of the nucleic acid sequences encoding PDE10A in the genome; or (ii) a nucleic acid incorporated into a vector or into the genomic DNA of an organism such that the resulting molecule is not identical to any naturally-occurring vector or genomic DNA. A representative PDE10A nucleic acid is provided in GenBank Accession No. NM_001130690.2. Nucleic acids also can include fragments of PDE10A nucleic acid sequences. As used herein, fragments refer to nucleic acids or polypeptides corresponding to less than an entire PDE10A sequence. Nucleic acid fragments may include those fragments of about 10 to 50 nucleotides in length, fragments of about 20 to 100 nucleotides in length, or fragments that are 100 to several hundred nucleotides in length. Such fragments may, for example, encode a PDE10Apolypeptide fragment, or have utility as hybridization probes or amplification primers.

Also provided herein are vectors containing a nucleic acid encoding a PDE10A polypeptide. Vectors also can include elements necessary for expression operably linked to a nucleic acid sequence encoding a PDE10A polypeptide. "Elements necessary for expression" include promoter sequences, and additionally may include regulatory elements, such as enhancer sequences, response elements or inducible elements that modulate expression of a PDE10A nucleic acid sequence. As used herein, "operably linked" refers to positioning of a promoter and/or other regulatory element(s) in a construct relative to a nucleic acid sequence encoding a PDE10A polypeptide in such a way as to direct or regulate expression of the nucleic acid. Such constructs are commercially available (e.g., expression vectors) and/or produced by recombinant DNA technology methods routine in the art. The choice of expression systems depends upon several factors, including, but not limited to, replication efficiency, selectability, inducibility, targeting, the level of expression desired, ease of recovery and the ability of the host to perform post-translational modifications.

As used herein, the term "host" or "host cell" includes not only prokaryotes, such as *E. coli*, but also eukaryotes, such as yeast, insect, plant and animal cells. Animal cells include, for example, COS cells and HeLa cells. A host cell can be transformed or transfected with a DNA molecule (e.g., a vector or construct) using techniques such as calcium phosphate or lithium acetate precipitation, electroporation, lipofection and particle bombardment. Host cells containing a vector as described herein may be used for purposes such as propagating the vector, producing PDE10A nucleic acid (e.g., DNA, RNA, antisense RNA), or expressing a PDE10A polypeptide or fragments thereof.

Methods of producing PDE10A polypeptides are provided. Methods of producing PDE10Apolypeptides include, but are not limited to, culturing host cells containing a expression vector under conditions permissive for expression of PDE10A and recovering (e.g., purifying) the PDE10A polypeptides. Methods of culturing bacteria and recovering expressed polypeptides, including insoluble polypeptides, are well known to those of ordinary skill in this art.

Methods of Treatment

A mammal having a PDE10A-antibody related autoimmune neurological disorder, in the presence or absence of cancer (and in the presence or absence of immune checkpoint inhibitor therapy for cancer), can be treated as described herein. For example, steroids for a patient with a PDE10A-antibody related autoimmune neurological disorder can be administered to a mammal once or multiple times over a period of time ranging from days to months. During treatment with an immune checkpoint inhibitor, the presence or absence of PDE10A specific autoantibodies can be monitored in a biological sample from the mammal being treated, as described herein. In some cases, one or more therapeutic compounds (e.g., immune checkpoint inhibitor and/or steroid) can be formulated into a pharmaceutically acceptable composition for administration to a mammal. For example, a therapeutically effective amount of a therapeutic compound can be formulated with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing one or more therapeutic compounds can be designed for oral or parenteral (including subcutaneous, intramuscular, intravenous, and intradermal) administration. When being administered orally, a pharmaceutical composition can be in the form of a pill, tablet, or capsule. Compositions suitable for parenteral administration include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

In some cases, a pharmaceutically acceptable composition including one or more therapeutic compounds can be administered locally or systemically. For example, a composition provided herein can be administered locally by intravenous injection or blood infusion. In some cases, a composition provided herein can be administered systemically, orally, or by injection to a mammal (e.g., a human).

Effective doses can vary depending on the severity of the cancer or movement disorder, the route of administration, the age and general health condition of the subject, excipient usage, the possibility of co-usage with other therapeutic treatments, and the judgment of the treating physician.

An effective amount of a composition containing one or more therapeutic compound can be any amount that reduces one or more symptoms of the condition being treated, without producing significant toxicity to the mammal. With cancer, for example, an effective amount can reduce the progression rate of the cancer, increase the progression-free survival rate, or increase the median time to progression. With a movement disorder or other neurological autoimmunity, an effective amount can reduce one or more symptoms such as improve hyperkinetic movements, enhance hypokinetic movement symptoms (e.g., parkinsonism), improve memory problems and confusion, and/or improve walking and pain. For example, an effective amount of an therapeutic compound can be from about 0.25 mg/kg to about 100 mg/kg (e.g., from about 0.3 mg/kg to about 11 mg/kg, from about 1 mg/kg to about 10 mg/kg, from about 2 mg/kg to about 10 mg/kg, from about 5 mg/kg to about 10 mg/kg, from about 6 mg/kg to about 10 mg/kg, from about 6 mg/kg to about 8 mg/kg, or from about 7 mg/kg to about 9 mg/kg). In some cases, from about 100 mg to about 1000 mg (e.g., from about 100 mg to about 250 mg, from about 125 mg to about 275 mg, from about 250 mg to about 1000 mg, from about 300 mg to about 1000 mg, from about 400 mg to about 1000 mg, from about 100 mg to about 900 mg, from about 100 mg to about 800 mg, from about 400 mg to about 800 mg, or from about 500 mg to about 700 mg) of a therapeutic compound can be administered to an average sized human (e.g., about 75-85 kg human) per administration (e.g., per daily or weekly administration) for about two to about twelve weeks. In some cases, a therapeutic compound can be administered daily within one of these dose ranges for a period of time (e.g., 14 or 21 days) followed by a seven-day rest period.

If a particular mammal fails to respond to a particular amount, then the amount of a therapeutic compound can be increased by, for example, two fold. After receiving this higher amount, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition may require an increase or decrease in the actual effective amount administered.

The frequency of administration of a therapeutic compound can be any amount that reduces the symptoms of the condition being treated without producing significant toxicity to the mammal. For example, the frequency of administration of a therapeutic compound can be from about once a day to about once a month (e.g., from about once a week to about once every other week). The frequency of administration of a therapeutic compound can remain constant or can be variable during the duration of treatment. A course of treatment with a composition containing a therapeutic compound can include rest periods. For example, a composition containing one or more immune checkpoint inhibitors can be administered daily over a two-week period followed by a two-week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition may require an increase or decrease in administration frequency.

An effective duration for administering a composition containing one or more therapeutic compounds can be any duration that reduces the symptoms of the condition being treated within without producing significant toxicity to the mammal. In some cases, the effective duration can vary from several days to several months. In general, the effective duration can range from about six weeks to about six months. Multiple factors can influence the actual effective duration used for a particular treatment. For example, an effective duration can vary with the frequency of administration, effective amount, use of multiple treatment agents, route of administration, and severity of the condition being treated.

The invention will be further described in the following examples, which do not limit the scope of the invention described in the claims.

Examples

Patients

The Mayo Clinic Neuroimmunology Laboratory database (>400,000 samples tested by indirect immunofluorescence assay (IFA) using murine tissue) was interrogated for samples with predominant basal ganglia staining. Twenty-one specimens with available quantities were identified and retested by indirect IFA using murine tissue. Six serum and two cerebrospinal fluid (CSF) specimens were identified from five patients that yielded a similar distinctive IgG staining pattern when applied to murine brain. Two more patients (one serum and two CSF specimens) were identified prospectively (total seven sera and four CSFs). Clinical information was abstracted from electronic files (one patient) or provided by referring physicians (six patients). Control sera included: 33 healthy subjects, 10 Huntington disease patients, four with autoimmune CRMPS-related-chorea and 54 with carcinomas (seven squamous-cell, 15 lung adenocarcinomas, 31 renal-cell, one of them treated with immune checkpoint inhibitors and one with renal and squamous-cell) with or without neurological autoimmunity.

Tissue Indirect Immunofluorescence Assay and Immunohistochemistry

Patients' specimens were tested on murine tissue cryosections at screening dilutions of 1:240 (serum; preabsorbed with liver powder) or 1:2 (CSF). See, Basal et al., *Neurology* 2018; 91: e1677-e1689. The antibody specific for human PDE10A was a rabbit polyclonal from Invitrogen (Catalog #PAS-31293). Secondary antibodies (from Southern Biotech, FITC-labeled goat anti-human IgG and anti-rabbit IgG and TRIC-labeled goat anti-human IgG) were used at 1:200 dilution.

Briefly, sections were fixed with 4% paraformaldehyde for one minute, washed with phosphate buffered saline (PBS), permeabilized with 0.5% CHAPS ($C_{32}H_{58}N_2O_7S$) for 1 minute, and washed with PBS. Normal goat serum (10% diluted in PBS) was applied for 1 hour and then sections were incubated with patient serum or CSF for 40 minutes, washed, incubated with secondary antibodies for 30 min and washed.

Formalin-fixed paraffin embedded sections (5 μm) of renal-cell carcinoma from patient four and normal human kidney were stained immunohistochemically using the polyclonal PDE10A antibody (1:500 dilutions) with overnight incubation at 4° C.

Protein Characterization

Antigen preparation. Porcine basal ganglia were identified macroscopically, dissected, frozen and stored at −80° C. Immunoreactivity of patients' sera was confirmed in cryosections by an IFA. Cytoplasmic and membrane extraction fractions were prepared. In brief, homogenized tissue (250 mM sucrose, 50 mM Tris-HCl [pH 7.4], 5 mM MgCl, 1 mM DTT and protease-inhibitor tablets [cOmplete™, Mini, by Sigma-Aldrich]) was centrifuged at 800 g twice to remove nuclei. The clarified supernatant (after centrifugation at 100,000 g) was stored at −80° C. (cytoplasmic fraction). The pellet was extracted for 1 hour (20 mM Tris-HCl [pH 7.8], 0.4M NaCl, 15% glycerol, 1.5% Triton-X, 1 mM DTT and protease-inhibitors), centrifuged at 10,000 g and the supernatant (membrane extraction fraction) was stored at −80° C. Immunoreactivity with patients' sera was found in both fractions by Western blot (WB), but was more intense in the membrane fraction that was used for further antigen characterization experiments.

Antibody purification and protein characterization. Patients' IgG was purified using protein G bound to magnetic beads (Dynabeads; Invitrogen) and incubated with the pig basal ganglia membrane extraction. IgG and bound protein were eluted and dissociated by boiling in SDS sample buffer and separated by gel electrophoresis. Silver staining and WB were used to identify the immunoreactive bands that were subsequently sequenced by mass spectrometry. To confirm that the immunoreactive bands contained the antigen yielding the tissue IFA pattern, the IgGs were eluted from excised nitrocellulose bands of corresponding molecular weight and the eluents tested by tissue IFA.

Specific Protein-Target Confirmation Assays

Western blot. Commercially available recombinant human PDE10A protein (Abcam, ab198428; 48% purity, expected MW 116 kDa) was used for WB to confirm the patients' antibody immunoreactivity.

Absorption of patient serum IgGs with recombinant PDE10A. Three patients' sera and a control serum (positive for PCA-1, also known as anti-Yo) were incubated overnight with either 2 μg of recombinant PDE10A or PBS and tested by IFA.

Cell-based immunofluorescence assays. HEK293 cells were transiently transfected with plasmids encoding either PDE10A1 or PDE10A2 isoforms (Genscript, reference sequence: NM_001130690.2 and NM_006661.3), fixed and tested by IFA. Patient sera and CSFs (1:200 and 1:5 dilutions, respectively) and PDE10A rabbit polyclonal commercial antibody (1:300 dilution) were applied, and secondary antibodies were used as above. All patient and control specimens yielded the same results, regardless of the PDE10A isoform used.

Antigen Characterization

All patients' specimens yielded the same synaptic immunofluorescence pattern of IgG binding, with prominent staining of the basal ganglia and related nuclei, to a lesser extent the hippocampus, and faint staining of the cerebellar granular layer (FIGS. 1A-C). None of the >400,000 clinical samples tested in the same period had similar staining.

WB of patients' sera using pig basal ganglia extracts revealed a common band (approximate MW 75 kDa) in three patients (FIG. 1D). IgG eluted from the nitrocellulose-corresponding band demonstrated the same staining pattern by tissue-IFA as the patients' serum (FIG. 1E), but not IgG eluted from a control band (~150 kDa). Eluents derived from immunoprecipitation experiments using purified IgG (patients one and four, and one healthy control) were treated by in-gel digestion and proteins were identified by mass spectrometry. The majority of peptides identified from the excised gel bands of the two patients but not of the control, corresponded to fragments of PDE10A (MW in pig: 79 kDa), including from a second common band above 200 kDa.

Confirmation of PDE10A as Autoantigen

PDE10A was confirmed as the pertinent antigen (FIGS. 2A-D). Firstly, there was co-localization on murine brain IFA of all patients' specimens with the PDE10A-specific antibody by confocal microscopy. Secondly, IgG in patients' sera bound to recombinant PDE10A in WB testing, while normal controls were negative. Thirdly, pre-absorption of serum from patients three, four, and five (but not from a patient harboring PCA-1) with recombinant PDE10A protein eliminated the specific IFA staining. Lastly, all specimens were positive by indirect immunofluorescence on PDE10A-transfected HEK cell-based assays (CBA), both with PDE10A1 and PDE10A2 isoforms. All controls were negative except for one patient with renal adenocarcinoma and aquaporin-4-IgG-seropositive neuromyelitis optica that had faint reactivity on PDE10A-transfected cells by CBA but was negative for the characteristic tissue IFA staining and recombinant PDE10A WB.

Clinical Characteristics

The patients' clinical characteristics are summarized in Table 1. The patients' median age was 70 years old (range 66-76 years); four were male (57%). Neurological information was available in six cases, although limited in four. Three patients had hyperkinetic movements (chorea, generalized dystonia and choreiform movements, right hemiballismus). One additional patient had parkinsonism. Four patients had encephalopathy, two of whom had meningeal carcinomatosis.

All patients had confirmed carcinomas, except for patient two in whom a lung nodule alone was radiologically detected. Carcinomas encountered were pulmonary non-small-cell type (one adenocarcinoma, one squamous-cell, one poorly-differentiated mesenchymal), two metastatic renal-cell and one pancreatic.

Two patients developed neurological symptoms a median of 4.5 months (range, 4-5) after initiation of immune checkpoint inhibitors (ICI) therapy targeting PD-1 for adenocarcinoma of kidney and lung. Both patients had hyperkinetic movement disorders and basal ganglial FLAIR/T2 hyperintensities (non-enhancing) on MRI that recapitulated the appearance of patient-IgG staining observed on mouse brain by IFA (FIG. 1F). This MRI finding was not reported in other patients with imaging data, but the imaging was not available for review by the authors. Both patients had CSF-restricted oligoclonal bands.

Only these two patients received immunotherapy. Patient four improved after a course of intravenous methylprednisolone and pembrolizumab cessation, but the benefit eventually subsided; sustained improvement occurred after tetrabenazine and craniocervical botulinum toxin injections. The patient was alive three years after diagnosis of a plurimetastatic renal-cell adenocarcinoma. Patient five, who developed hemiballismus while on ICI for lung adenocarcinoma, had no response to any immunotherapy. She died of neurological complications soon after the onset of her symptoms (Table 1). Of the remaining, three died shortly after neurological symptom onset (patients one, three, and six), or was lost to follow-up (patient two).

Immunohistochemical Testing of Renal Tissues for PDE10A

Figure 3:
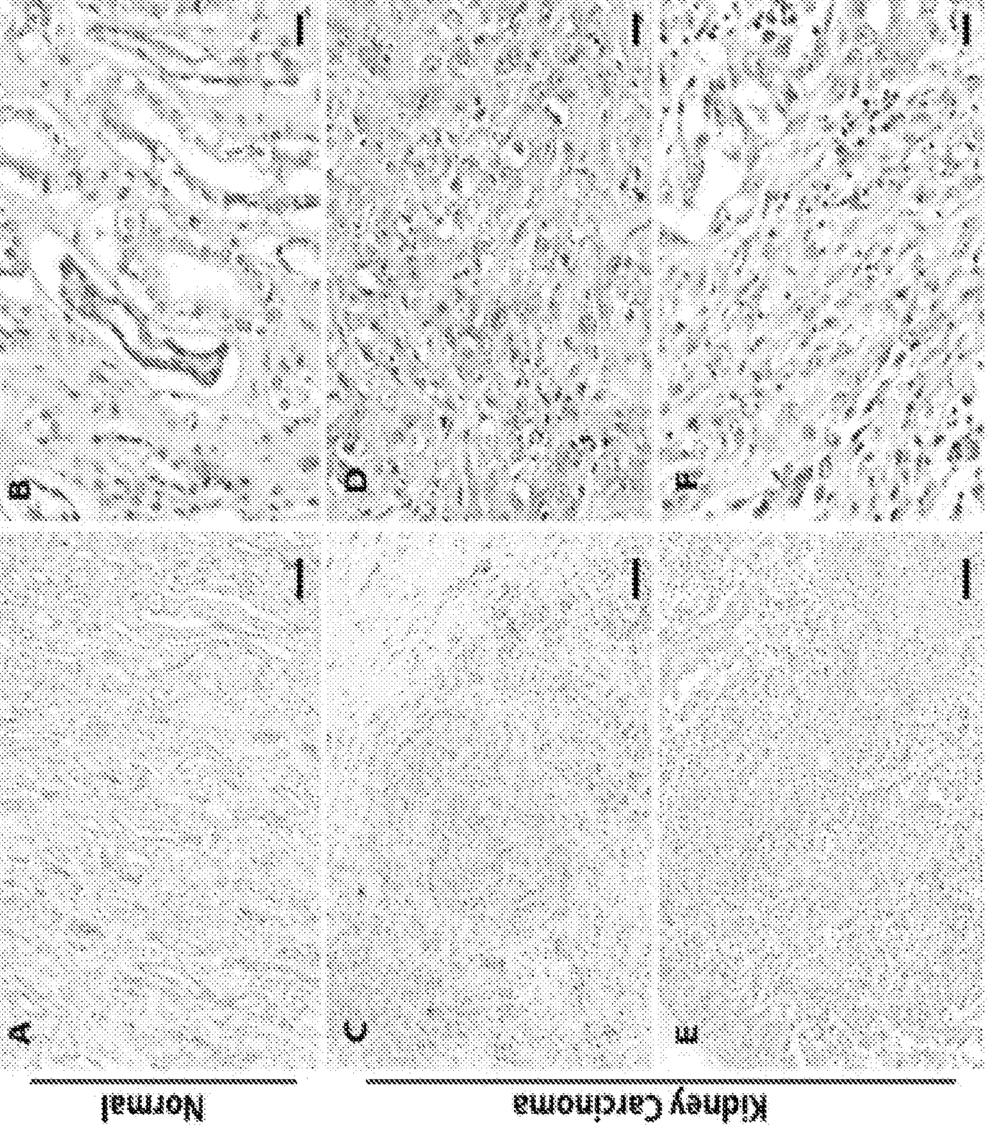
FIGS. 3A-3F. Immunohistochemistry of renal cell carcinoma (patient 4). PDE10A immunohistochemistry in normal control human kidney tissue (A,B). The high power image (B) indicates the collecting tube epithelium with marked expression of PDE10A. The kidney carcinoma tissue of patient 4 shows foci of variable PDE10A immunoreactivity: moderate expression (C, D) or scant PDE10A expression (E,F) in different parts of the tumor. Scale bars in A, C and E=100 μm. Scale bars in B, D, and F=20 μm.

PDE10A-specific-IgG produced diffuse staining of patient 4's renal adenocarcinoma (FIGS. 3C-F) while normal kidney tissue showed PDE10A expression restricted to tubular epithelium (FIGS. 3A-B).

TABLE 1

Patients with confirmed PDE10A autoimmunity

| | Main neurologic symptoms | Cancer | Cancer treatment | PDE10A-IgG | CSF | MRI | Treatment/Outcome |
|---|---|---|---|---|---|---|---|
| 1/M/71* | Not available | Right lung poorly differentiated mesenchymal neoplasm. | N/A | Serum titer: >1:30720 (CSF N/A) | N/A | Age appropriate changes reported | Death (no data available) |
| 2/M/75* | Chorea and encephalopathy | Lung nodule; no follow-up | N/A | Serum titer: 1:15360 (CSF N/A) | N/A | N/A | N/A |
| 3/F/69* | Encephalopathy (confusion) and dysarthria. | Squamous cell lung cancer; remote history of large meningioma radiated | N/A | Serum Titer: 30720 (CSF N/A) | N/A | N/A | Death (no data available) |
| 4/F/76 | Generalized hyperkinetic movement disorder (chorea, dyskinesia), dysarthria and dysphagia | Metastatic renal cell carcinoma (vena cava, brain, liver), | 5 months after onset of pembrolizumab treatment | Serum titer: >1:30720 & CSF: titer N/A | WBCs ≤5, Pro, 44 mg/dl, 8 OCBs | Flair/T2 BG hyperintensities | Pembrolizumab cessation; IVMP → improvement of the movement disorder. Not sustained, no response to PLEX or oral steroids. Cancer remission for 3 years. |
| 5/F/66 | Right hemiballismus and dysarthria | Lung adenocarcinoma | 4 months after onset of nivolumab treatment | Serum titer >30720 & CSF titer: 1:4 | WBCs ≤5, Pro, 56 mg/dl, 14 OCBs | Flair/T2 BG hyperintensities | Nivolumab cessation; IVMP, PLEX, IVIG, RTX → no improvement; death soon after from neurological deterioration |
| 6/M/70* | Parkinsonism, encephalopathy (confusion) | Metastatic renal cell carcinoma with probable leptomeningeal carcinomatosis | N/A | Serum & CSF; titers N/A | N/A | Leptomeningeal enhancement | Death (no data available) |
| 7/M/69* | Subacute ataxia, encephalopathy (hearing loss, headache and confusion) | Metastatic pancreatic adenocarcinoma (liver, lung, and probable meningeal carcinomatosis) | N/A | CSF titer: 1:64 (serum N/A) | N/A | Leptomeningeal enhancement | Death from cancer complications (no data available) |

*Patients with limited clinical information

Abbreviations: BG, basal ganglia; IVIG, intravenous immunoglobulins; IVMP, intravenous methylprednisolone; N/A, not available; OCBs, oligoclonal bands; PLEX, plasma exchange; pro, protein; RTX, rituximab; WBCs, white blood cells. Normal values for CSF: pro, ≤35 mg/dL; OCBs, <4; WBC, ≤5/μL.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a mammal having a paraneoplastic movement disorder, wherein said method comprises:

(a) detecting the presence of an autoantibody specific for phosphodiesterase 10A (PDE10A) in a sample obtained from said mammal, and (b) administering a steroid to said mammal.

2. A method for treating a paraneoplastic movement disorder in a mammal having an autoantibody specific for phosphodiesterase 10A (PDE10A), wherein said method comprises:

administering, to said mammal, a steroid.

3. The method of claim 1, wherein said mammal is a human.

4. The method of claim 1, wherein sample is a tissue sample, a blood sample, a serum sample, a CSF sample, or a plasma sample.

5. The method of claim 2, wherein said mammal is a human.

* * * * *